United States Patent [19]

Hunger

[11] 4,041,036
[45] Aug. 9, 1977

[54] WATER-INSOLUBLE COLORANTS, PROCESS FOR PREPARING THEM AND THEIR USE

[75] Inventor: Klaus Hunger, Kelkheim, Taunus, Germany

[73] Assignee: Hoechst Aktiengesellschaft, Frankfurt am Main, Germany

[21] Appl. No.: 676,925

[22] Filed: Apr. 14, 1976

[30] Foreign Application Priority Data

Apr. 16, 1975 Germany .............................. 2516700

[51] Int. Cl.² .......................................... C07D 491/22
[52] U.S. Cl. ........................ 260/256.4 F; 260/251 A; 260/256.4 C; 260/256.5 R; 260/260
[58] Field of Search .................. 260/256.4 F, 256.5 R, 260/251 A, 260

[56] References Cited

U.S. PATENT DOCUMENTS 3,931,182   1/1976   Kast et al. ..................... 260/256.5 R

OTHER PUBLICATIONS

*Beilsteins Handbuch der Organischen Chemie,* 1950, pp. 419-420.
Vvedenskii, "Chemical Abstracts", vol. 72, 1970, col. 111406t.

*Primary Examiner*—Donald G. Daus
*Assistant Examiner*—James H. Turnipseed
*Attorney, Agent, or Firm*—Curtis, Morris & Safford

[57] ABSTRACT

The condensation of barbituric acid, thiobarbituric acid or imino-barbituric acid with 2-hydroxy-3-carboxy-1-naphthaldehydes or their arylamides in a solvent at 20° to 180° C yields colored compounds which are useful as pigments.

9 Claims, No Drawings

WATER-INSOLUBLE COLORANTS, PROCESS FOR PREPARING THEM AND THEIR USE

The present invention relates to compounds of the general formula I

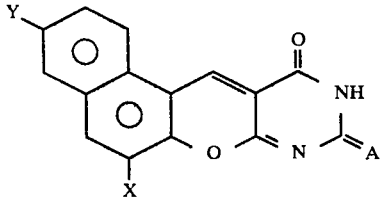

(I)

wherein A is oxygen or sulfur or the NH-group, X is the COOH group or the group -CONHAr, wherein Ar is the naphthyl group, a phenyl group, which may be substituted by 1 to 3 halogen atoms, alkyl, alkoxy, alkylsulfonyl, carbalkoxy, trifluoromethyl, nitro, cyano, alkanoylamino, benzoylamino, or carbamoyl or sulfamoyl groups which may be substituted at the nitrogen atom by one or two alkyl groups or a phenyl group, or Ar is the benzimidazolone, chlorobenzimidazolone, tetrahydrodioxo-quinazolindione, tetrahydrodioxo-quinoxalindione, phthalimide or tetrahydrodioxo-phthalazindione group and Y is hydrogen, chlorine or bromine or a methoxy group.

The terms "alkyl," "alkoxy" and "alkanoyl" here and in the following are groups containing 1 to 4 carbon atoms.

There are preferably used compounds of the general formula II

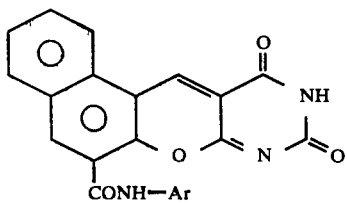

(II)

wherein Ar is a phenyl group which may be substituted by 1 to 3 alkyl, alkoxy, alkysulfonyl, carbalkoxy, trifluoromethyl, nitro, cyano, alkanoylamino, carbamoyl or sulfamoyl groups or bromine or chlorine atoms, or Ar represents the benzimidazolone or chlorobenzimidazolone group.

Ar is for example phenyl, o-, m-, p-tolyl, o-, m-, p-methoxyphenyl, o-, m-, p-ethoxyphenyl, o-, m-, p-chlorophenyl, o-, m-, p-bromophenyl, the o-, m-trifluoromethylphenyl, o-, m-, p-nitrophenyl, 2,34-dimethylphenyl, 2,5-dimethoxyphenyl, 2,4-dichlorophenyl, 2,5-dichlorophenyl, 2,4,5-trichlorophenyl, 2-chloro-3-methylphenyl, 2-chloro-4-methylphenyl, 2-chloro-5-methylphenyl, 3-chloro-2-methylphenyl, 4-chloro-2-methylphenyl, 2-methoxy-5-chlorophenyl, 2,5-dimethoxy-4-chlorophenyl, 2,4-dimethoxy-5-chlorophenyl, 2-methoxy-4-chloro-5-methylphenyl, 4-acetaminophenyl, 4-benzoylaminophenyl, 5-benzimidazolyl, 4-phthalimidyl, 6-(1,2,3,4-tetrahydro-2,3-dioxo)-quinoxalyl, 6-(1,2,3,4-tetrahydro-1,4-dioxo)-quinazolyl or 6-(1,2,3,4-tetrahydro-2.4-dioxo)-phthalazinyl.

The invention further relates to a process for preparing the compounds of the formula I, which comprises reacting a 2-hydroxynaphthaldehyde of the formula III

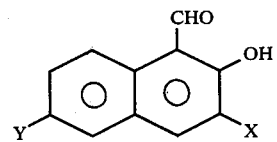

(III)

wherein X and Y have the meanings mentioned for the formula I, with a compound of the general formula IV

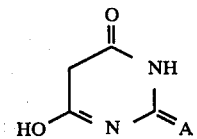

(IV)

wherein A has the meaning mentioned for the formula I, in a solvent or solvant mixture at temperatures between 20° and 180° C, preferably 80° to 150° C.

As solvents there are suitable for example lower aliphatic carboxylic acids, such as formic acid, acetic acid or propionic acid, alcohols, especially lower alkanols such as ethanol, propanol, isopropanol, butanol, or isobutanol; aromatic hydrocarbons such as benzene, toluene, xylene, chlorobenzene, dichlorobenzene or dipolar aprotic solvents such as dimethylformamide, dimethylsulfoxide, tetramethylenesulfone, N-methylpyrrolidone, or tetramethylurea or mixtures of preferably two or three of these solvents.

The reaction preferably proceeds at elevated temperatures within 30 minutes to 8 hours, preferably 1 to 4 hours, wherein the sparingly soluble reaction products are generally precipitated from the solution and can be isolated by filtering, washing and drying.

The reaction mixture preferably contains a lower aliphatic carboxylic acid which also effects a better solution of difficulty soluble reaction components. Furthermore, catalytical amounts of piperidine or ammonium acetate may help to accelerate the reaction. The condensation may also be carried out in the way that the water formed during the reaction is distilled off azeotropically.

Examples for the aldehydes of the formula III are:
1-Formyl-2-hydroxy-3-naphthoic acid anilide
1-Formyl-2-hydroxy-3-naphthoic acid -2'-chloroanilide
1-Formyl-2-hydroxy-3-naphthoic acid-4'-chloroanilide
1-Formyl-2-hydroxy-3-naphthoic acid-2',4'-dichloroanilide
1-Formyl-2-hydroxy-3-naphthoic acid-2', 5'-dichloroanilide
1-Formyl-2-hydroxy-3-naphthoic acid-2'-methylanilide
1-Formyl-2-hydroxy-3-naphthoic acid-4'-methylanilide
1-Formyl-2-hydroxy-3-naphthoic acid-2'-methoxyanilide 1-Formyl-2-hydroxy-3-naphthoic acid-2'-ethoxyanilide
1-Formyl-2-hydroxy-3-naphthoic acid-4'-methoxyanilide
1-Formyl-2-hydroxy-3-napthoic acid-4'-ethoxyanilide
1-Formyl-2-hydroxy-3-napthoic acid-2',4'-dimethylanilide
1-Formyl-2-hydroxy-3-naphthoic acid-2'-methyl-3'-chloroanilide
1-Formyl-2-hydroxy-3-naphthoic acid-2'-methyl-4'-chloroanilide
1-Formyl-2-hydroxy-3-naphthoic acid-2',5'-dimethoxyanilide
1-Formyl-2-hydroxy-3-naphthoic acid-2', 5'-dimethoxy-4'-chloroanilide
1-Formyl-2-hydroxy-3-naphthoic acid-2',4'-dimethoxy-5'-chloroanilide
1-Formyl-2-hydroxy-3-naphthoic acid-4'-acetaminoanilide
1-Formyl-2-hydroxy-3-naphthoic acid-4'-benzoylaminoanilide
1-Formyl-2-hydroxy-3-naphthoic acid-3'-trifluoromethylanilide
1-Formyl-2-hydroxy-3-naphthoic acid-2'-nitroanilide
1-Formyl-2-hydroxy-6-bromo-3-naphthoic acid anilide
1-Formyl-2-hydroxy-3-naphthoyl-5'-aminobenzimidazolone
1-Formyl-2-hydroxy-3-naphthoyl-5'-amino-7'-chlorobenzimidazolone
1-Formyl-2-hydroxy-3-naphthoyl-6'-amino-1',2',3',4'-tetrahydroquinazolindione-(2',4')
1-Formyl-2-hydroxy-3-naphthoyl-7'-amino-1',2',3',4'-tetrahydro-quinazolindione-(2',4')
1-Formyl-2-hydroxy-3-naphthoyl-6'-amino-1',2',3',4'-tetrahydro-2',3'-dioxo-quinoxaline
1-Formyl-2-hydroxy-3-naphthoyl-4'-aminophthalimide
1-Formyl-2-hydroxy-3-naphthoyl-6'-amino-1',2',3',4'-tetrahydro-1',4'-dioxo-phthalazine The invention further relates to the use of the compounds of the formula I as colorants. Due to their low solubility they are especially suitable as pigments.

To obtain the best possible pigmentary properties of the colorants it may be advantageous to convert the product into a finely divided form by heating it in a solvent, if desired in the presence of water or salt solutions.

Suitable solvents are those in which the colorants are insoluble but which allow under the finishing conditions a certain degree of (superficial) solution, for example aliphatic alcohols, especially lower alkanols such as ethanol, isopropanol, iso- or n-butanol, ketones such as methyl-isopropyl ketone or methyl isobutyl ketone, chlorinated aromatic hydrocarbons such as chlorobenzene, chlorotoluene or dichlorobenzenes, as well as dipolar aprotic solvents, for example dimethylformamide, dimethylacetamide, dimethyl sulfoxide, polyalkylureas, such as tetramethyl urea, N-methylpyrrolidone and phosphoric acid amides such as hexamethyl phosphoric acid trisamide.

The novel colorants represents valuable pigments which are suitable for printing inks, dispersion paints, lacquers and for the pigmentation of high molecular organic materials, as for example cellulose ethers and esters, polyamides, polyurethanes or polyesters, acetyl cellulose, nitrocellulose, natural or synthetic resins, for example aminoplasts, especially urea- and melamineformaldehyde resins, phenoplastis, polycarbonates, polyolefins, such as polyethylene or polypropylene, polystyrene, polyvinyl chloride, polyacrylonitrile, polyacrylic acid esters, rubber, casein, silicone oils and silicone resins, individually or in mixture with one another. It is not controlling if the high molecular compounds mentioned are plastic masses, melts, spinning solutions, lacquers or printing pastes. It may be advantageous to use the novel pigments as toners or in the form of preparations.

The novel compounds are especially characterized by brilliant shades, an excellent fastness to migration and to light and to a high heat stability.

The following Examples illustrate the invention.

EXAMPLE 1

18 g of 1-formyl-2-hydroxy-3-naphthoic acid-2',5'-dichloroanilide were dissolved under nitrogen cover in 200 ml of dimethylformamide. Then a solution of 6.4 g of barbituric acid in 100 ml of glacial acetic acid was added. After addition of 1 ml of piperidine the reaction mixture was heated to 115° C and kept for 4 hours at this temperature. After cooling to 70° C the product was suction-filtered and the reddish-yellow residue was washed with ethanol and water and dried. 12.4 g of the pigment of the formula

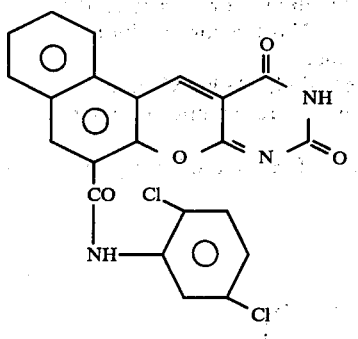

were obtained.

EXAMPLE 2

17.8 g of 1-formyl-2hydroxy-3-naphthoic acid-2'-methoxy-5'-chloroanilide were dissolved in 200 ml of glacial acetic acid and 50 ml of N-methylpyrrolidone at 125° C in a nitrogen atmosphere. Then 7.2 g of thiobarbituric acid were added. The temperature was kept for 5 hours at 125° C, then the mixture was cooled to 70° C and the precipitate was suction-filtered, washed with ethanol and water and dried.

16.2 g of the bluish red pigment of the formula

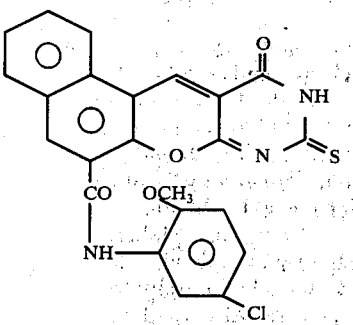

were obtained.

Further pigments of the formula I are obtained following the process indicated in the above Examples by condensation of a 1-formyl-2-hydroxy-3-naphthoic acid derivatives of the formula III with a cyclic compound of the formula IV.

TABLE 1

| Example | R | Shade |
|---|---|---|
| 3 | phenyl | yellow |
| 4 | 2-methoxyphenyl (CH₃O) | reddish yellow |
| 5 | 5-methylbenzimidazol-2(3H)-one | orange |
| 6 | 2-methylphenyl (CH₃) | yellow |
| 7 | 2-ethoxyphenyl (C₂H₅O) | greenish yellow |
| 8 | 4-methoxyphenyl (—OCH₃) | yellow |
| 9 | 2-chlorophenyl (Cl) | + greenish yellow |
| 10 | 2-nitrophenyl (NO₂) | greenish yellow |
| 11 | 2,5-dimethoxy-4-chlorophenyl (CH₃O, OCH₃, Cl) | reddish yellow |

TABLE 1-continued

| Example | R | Shade |
|---|---|---|
| 12 | 2-methoxycarbonylphenyl (COOCH₃) | yellow |
| 13 | 2-trifluoromethylphenyl (CF₃) | greenish yellow |
| 14 | 4-acetamidophenyl (NHCOCH₃) | reddish yellow |
| 15 | 5-methyl-2-acetamidophenyl | yellow |
| 16 | 5-methylquinoxaline-2,3(1H,4H)-dione | reddish yellow |
| 17 | 4-methylphthalhydrazide | greenish yellow |
| 18 | 5-methyl-7-chlorobenzimidazol-2(3H)-one | yellow |
| 19 | 2-chloro-5-methoxyphenyl (Cl, OCH₃) | reddish yellow |
| 20 | 2-methoxy-4-chloro-5-methoxyphenyl (OCH₃, Cl, OCH₃) | reddish yellow |
| 21 | 4-methylphenyl (CH₃) | reddish yellow |

TABLE 1-continued

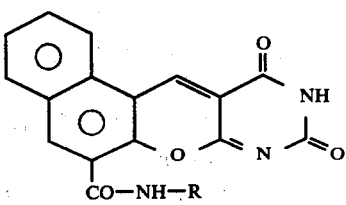

| Example | R | Shade |
|---|---|---|
| 22 | ![4-OC2H5 phenyl] | greenish yellow |
| 23 | ![3-methyl-4-chlorophenyl] | yellow |
| 24 | ![4-chlorophenyl] | greenish yellow |

TABLE 2

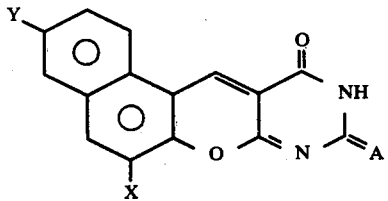

| Ex. | X | Y | A | Shade |
|---|---|---|---|---|
| 25 | —CO—NH—⟨4-Cl phenyl⟩ | Br | O | yellow |
| 26 | —CO—NH—⟨2-CH3, 4-Cl phenyl⟩ | H | NH | brown |
| 27 | —CO—NH—⟨2-CH3O, 4-Cl, 5-OCH3 phenyl⟩ | H | S | brown |
| 28 | —COOH | H | O | greenish yellow |

TABLE 2-continued

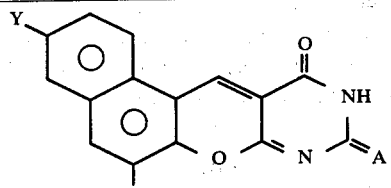

| Ex. | X | Y | A | Shade |
|---|---|---|---|---|
| 29 | CH3O, —CONH—⟨phenyl⟩ | Br | O | orange |
| 30 | —CONH—⟨phenyl⟩ | OCH3 | O | gelb |

I claim:

1. A compound of the formula

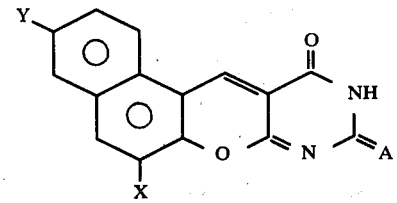

in which A is oxygen, sulfur or imino, Y is hydrogen, chlorine, bromine or methoxy and X is carboxy or a group of the formula —CO—NH—Ar, in which Ar is naphthyl; phenyl; phenyl substituted by 1 to 3 equal or different substituents selected from alkyl, alkoxy, alkylsulfonyl, carboalkoxy, trifluoromethyl, nitro, cyano, alkanoylamino, benzoylamino, carbamoyl mono- or di-N alkyl-carbamoyl, N-phenylcarbamoyl, sulfamoyl, mono- or di-N-alkyl-sulfamoyl, N-phenyl sulfamoyl and halogen; or Ar is benzimidazolonyl, chlorobenzimidazolonyl, tetrahydro-quinazoline-dionyl, tetrahydro-quinoxaline-dionyl, phthalimidyl or tetrahydrophthalazine-dionyl; wherein each alkyl, alkoxy and alkanoyl moiety has 1 to 4 carbon atoms.

2. A compound as claimed in claim 1, wherein A is oxygen, Y is hydrogen, X is —CO—NH—Ar, Ar standing for phenyl which is unsubstituted or substituted by 1 to 3 equal or different substituents selected from alkyl, alkoxy, alkylsulfonyl, carboalkoxy, trifluoromethyl, nitro, cyano, alkanoylamino, carbamoyl, sulfamoyl, chlorine and bromine, or Ar is benzimidazolonyl or chlorobenzimidazolonyl.

3. A compound as claimed in claim 1, wherein A is oxygen, Y is hydrogen, X is —CO—NH—Ar, Ar standing for phenyl which is unsubstituted or substituted by 1 to 3 equal or different substituents selected from methyl, methoxy, ethoxy, chlorine, nitro, carbomethoxy, trifluoromethyl and acetamino.

4. A compound as claimed in claim 1, wherein A is oxygen, Y is hydrogen, X is —CO—NH—Ar, Ar standing for phenyl substituted by 1 to 3 substituents selected from methoxy and chlorine.

5. The compound as claimed in claim 4, wherein Ar is 2,5-dichlorophenyl.

6. The compound as claimed in claim 4, wherein Ar is 2-anisyl.

7. The compound as claimed in claim 4, wherein Ar is 2,4-dimethoxy-5-chlorophenyl.

8. The compound as claimed in claim 4, wherein Ar is 2-methoxy-5-chlorophenyl.

9. The compound as claimed in claim 4, wherein Ar is 2,5-dimethoxy-4-chlorophenyl.

* * * * *